United States Patent [19]

Adams et al.

[11] 4,178,448
[45] Dec. 11, 1979

[54] PROCESS FOR PREPARING HERBICIDAL TRIAZINES

[75] Inventors: Charles D. Adams, Newark; Earl W. Cummins, Wilmington, both of Del.; Steven I. Gleich, Seabrook, Tex.

[73] Assignee: E. I. Du Pont de Nemours and Company, Wilmington, Del.

[21] Appl. No.: 895,587

[22] Filed: Apr. 12, 1978

Related U.S. Application Data

[63] Continuation-in-part of Ser. No. 777,324, Mar. 14, 1977, abandoned, which is a continuation-in-part of Ser. No. 675,921, Apr. 15, 1976, abandoned, which is a continuation-in-part of Ser. No. 574,351, May 5, 1975, abandoned.

[51] Int. Cl.² .......................................... C07D 251/46
[52] U.S. Cl. ...................................... 544/194; 544/211
[58] Field of Search ................................ 544/194, 211

[56] References Cited

U.S. PATENT DOCUMENTS

| | | | |
|---|---|---|---|
| 3,850,924 | 11/1974 | Fuchs et al. | 544/211 |
| 3,907,795 | 9/1975 | Tocker | 544/194 |
| 3,983,116 | 9/1976 | Lin | 544/211 |

*Primary Examiner*—John M. Ford

[57] ABSTRACT

An improved process for preparing 3-cyclohexyl-1-methyl-6-dimethylamino-s-triazine-2,4(1H,3H)dione by the following reaction sequence:

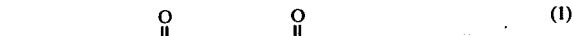

(1)

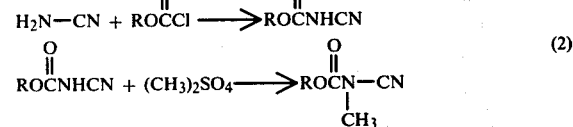

(2)

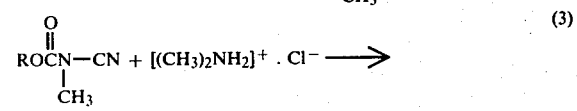

(3)

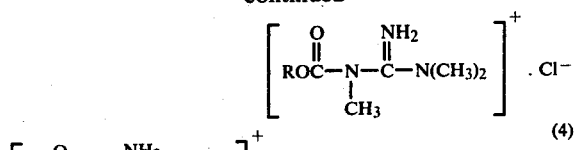

(4)

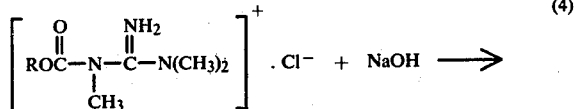

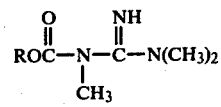

(5)

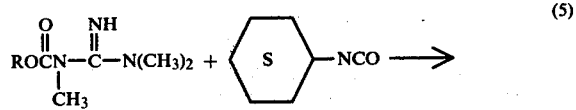

(6)

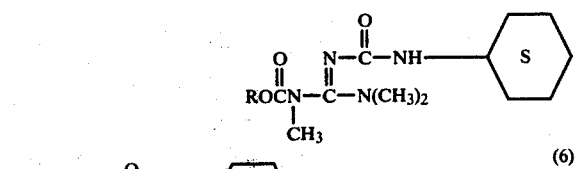

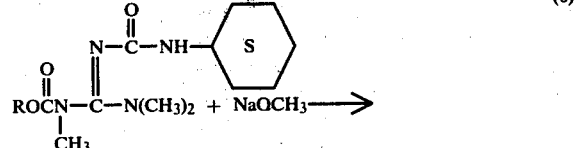

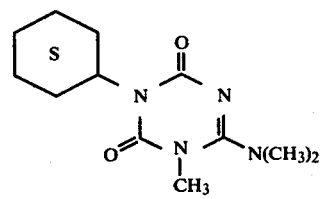

the improvement comprising using R=ethyl, n-propyl or isopropyl, preferably ethyl, thus permitting significantly higher practical overall yields.

Related 3-substituted-1-methyl-6-substituted amino-s-triazine-2,4(1H,3H)diones and 4-thio-2,4(1H,3H)-diones are prepared similarly. These products are useful as herbicides.

15 Claims, 1 Drawing Figure

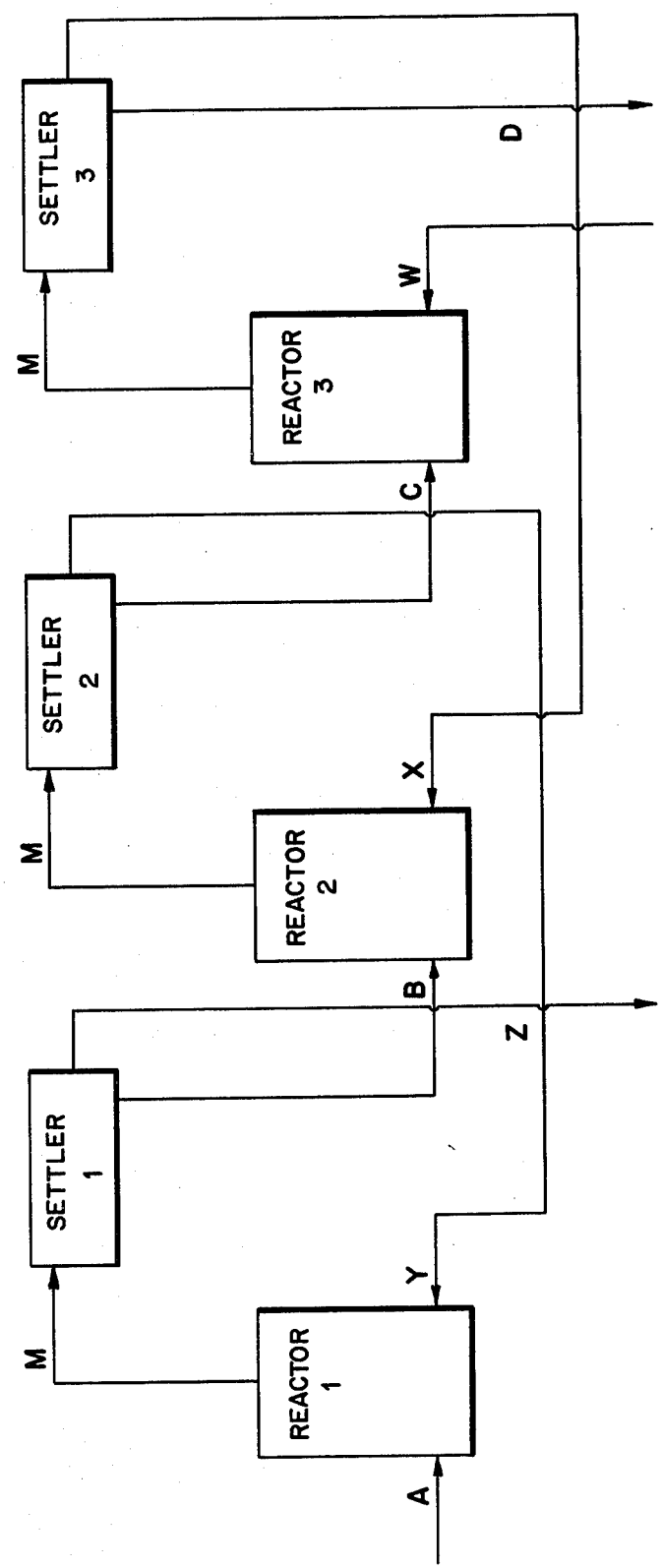

PROCESS FOR PREPARING HERBICIDAL TRIAZINES

CROSS-REFERENCE TO RELATED APPLICATIONS

This application is a continuation-in-part of copending U.S. Patent Application Ser. No. 777,324, filed Mar. 14, 1977 now abandoned, which is a continuation-in-part of U.S. Patent Application Ser. No. 675,921, filed Apr. 15, 1976, and now abandoned, which is, in turn, a continuation-in-part of U.S. Patent Application Ser. No. 574,351, filed May 5, 1975, and now abandoned.

BACKGROUND OF THE INVENTION

U.S. Pat. No. 3,657,443, filed Sept. 29, 1969, by Hein Louis Klopping, and granted Apr. 18, 1972, discloses the preparation of alkoxycarbonylcyanamides (alkyl-cyanocarbamates) from cyanamide and alkyl chloroformates.

Berichte, 62, 1393–1394 (1929) discloses the reaction of the ethoxycarbonylcyanamide with dimethylsulfate to produce N-ethoxycarbonyl-N-methylcyanamide.

U.S. Pat. No. 3,823,179, filed Dec. 7, 1972, by Julius Jakob Fuchs, and granted July 9, 1974, discloses the reaction of N-alkoxycarbonyl-N-methylcyanamides with amine hydrochlorides followed by extraction with methylene chloride, evaporation of methylene chloride under vacuum, distillation, and subsequent reaction with isocyanate or isothiocyanate. However, the only specific examples are to instances where the alkoxy group is a methoxy group. And in the generic segment of the specification, the only disclosed process for achieving alkoxycarbonylmethylcyanamides where the alkoxy group is other than methyl is by starting with alkyl cyanamides.

U.S. Pat. No. 3,850,924, filed Apr. 5, 1973, by Julius J. Fuchs and Joel B. Wommack, and granted Nov. 26, 1974, discloses a process for making 3-cyclohexyl-1-methyl-6-dimethylamino-s-triazine-2,4(1H,3H)-dione by the following reaction sequence:

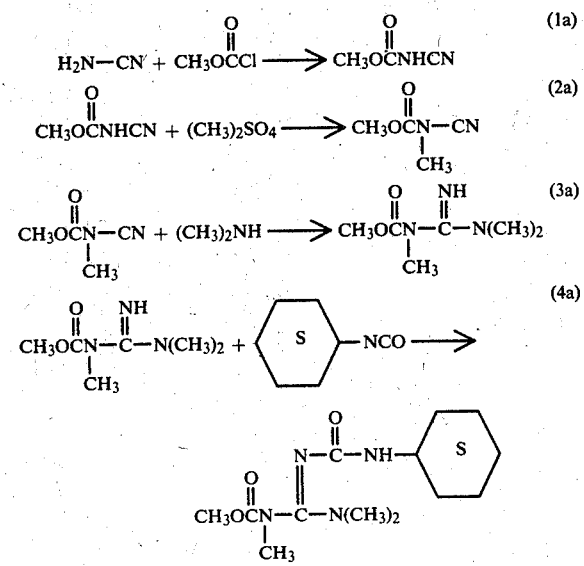

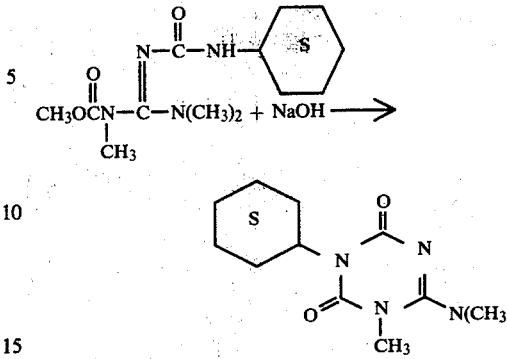

It has now been discovered that significant increases in the overall yield of the above-described five-step reaction sequence, and in particular, in the practical yield of said reaction sequence, can be achieved by using a chloroformate of the formula:

where R=ethyl, n-propyl, or isopropyl, preferably ethyl.

SUMMARY OF THE INVENTION

This invention is an improvement in the process for the preparation of compounds of the formula:

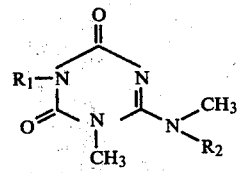

wherein
$R_1$ is $C_2$-$C_8$ alkyl, $C_5$-$C_8$ cycloalkyl, norbornyl, methylcyclohexyl, methylcyclopentyl, phenyl, or chlorophenyl; and
$R_2$ is $C_1$-$C_4$ alkyl;

by the reaction sequence as described in said U.S. Pat. No. 3,850,924 and summarized above in equations (1a) through 5(a), wherein one of the more significant improvements comprises replacing methyl chloroformate with an alkyl chloroformate of the formula:

where R is ethyl, n-propyl, or isopropyl and reacting with cyanamide as the first step in said above reaction sequence and carrying said alkyl group R through each of the remainder of the steps in said reaction sequence. Additional significant improvements comprise conducting the cyclization step in the absence of dimethylamine and removing by-product alkanol from the reaction medium by vaporization therefrom substantially as it is formed.

Thus, the improved process of the present invention comprises the following steps in sequence:

(a) contacting cyanamide with an alkyl chloroformate of the formula:

wherein R=$C_{2-3}$ alkyl, to form the corresponding alkoxycarbonylcyanamide;

(b) contacting an alkylating agent of the formula $CH_3Z$, wherein Z=I, Br or

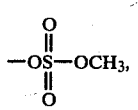

with the alkoxycarbonylcyanamide to form N-alkoxycarbonyl-N-methylcyanamide;

(c) contacting the product of step (b) with the amine hydrochloride or amine sulfate of the formula:

$[H_2N(CH_3)R_2]_n^{\oplus} \cdot Y^{\ominus n}$, wherein Y=$Cl^-$ or $SO_4^{--}$ and n=1 when Y is $Cl^-$ and n=2 when Y is $SO_4^{--}$, to form a compound of the formula:

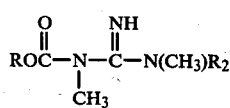

(d) contacting the product of step (c) with an alkali metal hydroxide to form a compound of the formula $$ROC(O)-N(CH_3)-C(NH)-N(CH_3)R_2 \quad IV$$

(e) removing unreacted amine, $HN(CH_3)R_2$, from the reaction mass resulting from step (d);

(f) contacting the formula IV product of step (d) with an isocyanate of the formula $R_1NCO$ to form a compound of the formula:

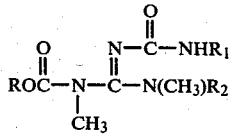

(g) contacting the formula V product of step (f) with an alkali metal alkoxide or hydroxide and removing the by-product alkanol from the reaction medium by vaporization therefrom substantially as it is formed to form a compound of the formula:

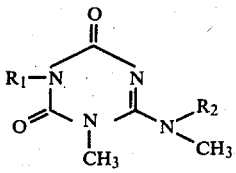

DETAILED DESCRIPTION OF THE INVENTION

The improved process of this invention comprises the corresponding reactions of equations I through VI below. Equation I represents preparation of the starting material as described in U.S. Pat. No. 3,657,443.

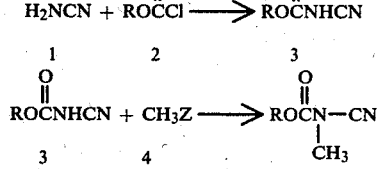

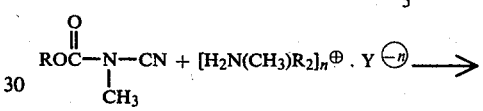

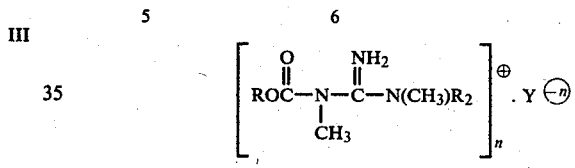

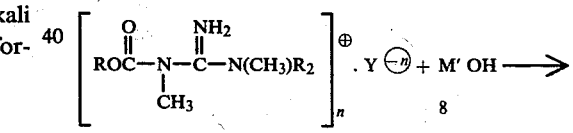

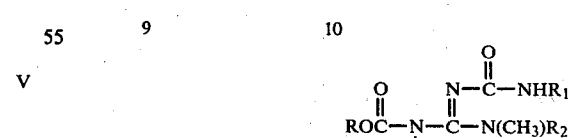

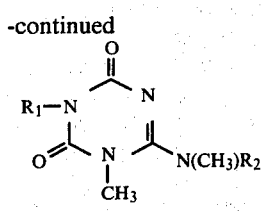

13 wherein

R is ethyl, n-propyl, or isopropyl;

$R_1$ is selected from alkyl of 2-8 carbon atoms, cycloalkyl of 5-8 carbon atoms, norbornyl, methylcyclopentyl, methylcyclohexyl, phenyl, and chlorophenyl;

$R_2$ is alkyl of 1-4 carbon atoms;

Y is $Cl^-$ or $SO_4^{--}$; $n=1$ when Y is $Cl^-$ and $n=2$ when Y is $SO_4^{--}$;

Z is iodide, bromide or

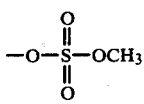   VI

M' is alklai metal; and $R_3$ is hydrogen or alkyl of 1-4 carbon atoms.

As used herein, the term "practical yield" represents the ratio of the amount of compound recovered and carried forward in the process relative to the theoretical amount of the compound which could be formed at 100% conversion of the starting materials. The difference between 100% yield and the practical yield represents not only incomplete conversion of starting materials and loss to side reactions, but also solubility and other physical losses in discarded process fluids.

Steps I and II are performed sequentially in water. Compound 5 is isolated by separating it from the aqueous brine formed in these reactions. The solubility in brine of those compounds 5 where R is ethyl, n-propyl or isopropyl is significantly lower than that of N-methoxycarbonyl-N-methylcyanamide. Thus, a greater recovery of compound 5 results, substantially increasing the practical yield of step II and the six-step process in general.

After the reaction of step III is completed, compound 7 and any unreacted compound 6 must be converted to the free base forms with an alkali metal hydroxide. The unreacted amine, $HN(CH_3)R_2$, must be removed so that it will not be present in step V, where it would react with the isocyanate and would result in serious yield loss and in impurities in the final product. The unexpected increase in practical yield, when R is ethyl, n-propyl, or isopropyl rather than methyl, is particularly signficant during this removal of the unreacted amine from aqueous alkaline solution by distillation or by extraction followed by distillation. Stability of compound 9 under these conditions is considerably greater when R is ethyl, n-propyl, or isopropyl than when R is methyl. Thus, the practical yield of the process is significantly enhanced.

In addition, still further significant increase in practical yield results from the extraction process. The compound 9 when R=methyl has a low distribution coefficient between the extraction solvent, preferably toluene, and the reaction mass, thus making extraction of the methyl compound impractical on a commercial scale. However, it has now been discovered that the distribution coefficient for the ethyl, n-propyl, and isopropyl analogs are significantly higher, thus permitting commercially practical recovery of product by extraction.

In the following detailed description, all temperatures are in degrees centrigrade and all percentages are by weight unless otherwise stated.

An aqueous solution of the sodium salt of compound 3 containing from 15-35% of compound 3, preferably 20-30%, is reacted at 10°-70°, preferably 25°-30°, with 0.9-2.0, preferably 1.2-1.3, molecular equivalents of an alkylating agent 4 (for example, dimethyl sulfate) during a period of 1-16 hours, preferably 2-4 hours (equation II). Methyl iodide or bromide can be used instead of dimethyl sulfate; the sulfate is preferred for economic reasons.

As the reaction proceeds, a second phase of compound 5 forms. After the reaction has proceeded for the desired time, the upper layer is separated and the lower aqueous layer can be discarded, or if economic conditions justify, this layer can be extracted with an organic solvent, preferably toluene, or distilled to recover the small amount of compound 5 contained therein.

When Z is

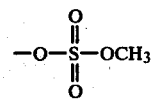

the yield from step II is significantly higher when performed in a sequential or cascaded fashion rather than in a single batch. The difference between a single batch reaction system and a cascaded reaction system is that in a single batch system, all the reaction is carried out in a single reactor during one unbroken hold period, while in a cascaded system only a part of the reaction is completed in any individual reactor or during any individual hold period. Cascaded systems can use either batch or continuous reactors. They can be simple mechanically or complex.

A reactor and a storage tank can be used for a simple cascaded batch system. To begin Batch 1, compounds 4 and 3, sodium salt are charged to the Step II reactor. After only ½ of the normal single batch hold period, the layers are settled. The bottom aqueous layer is drained off and discarded while the upper organic layer is left in the reactor. Fresh compound 3, sodium salt is charged to the reactor and the mixture is again stirred for ½ of the normal hold period. After settling, the lower aqueous layer is drained to the storage tank while the upper organic layer of compound 5 is discharged into the Step III reactor. This ends Batch 1. To begin Batch 2, the retained aqueous layer is returned from the storage tank to the Step II reactor and fresh compound 4 is charged. After ½ the normal hold period, the lower aqueous layer is drained off and discarded while the upper organic layer is left in the reactor. Fresh compound 3, sodium salt is added and the mixture is again stirred for ½ of the normal hold time. The lower aqueous layer is drained to the storage tank and saved for Batch 3 while the upper layer of compound 5 is discharged to the Step III reactor. This ends Batch 2. The cycle can be repeated as many times as necessary. More stages could be obtained, if desired, by adding additional reactors and storage tanks.

A novel continuous cascaded reaction system is shown in THE FIGURE. The letters describe the following process streams:

A compound 3, sodium salt solution
B partially reacted compound 3, sodium salt solution
C partially reacted compound 3 sodium salt solution
D completely reacted compound 3, sodium salt solution
W compound 4 (dimethyl sulfate)
X mixture of dimethyl sulfate and compound 5
Y mixture of dimethyl sulfate and compound 5
Z compound 5 product
M mixture of aqueous and organic phases.

The aqueous and organic layers enter into the bottom of each reactor and the mixture flows upward under plug-flow conditions. The mixture discharges from the top of the reactor into the settler where the phases are allowed to separate. During continuous operation, compound 3, sodium salt continuously enters Reactor 1, and compound 4 continuously enters Reactor 3. Product 5 is continuously withdrawn from Settler 1 and spent aqueous layer is continuously withdrawn from Settler 3.

Compound 5 is added to an aqueous solution containing 15–75% of the amine hydrochloride or 15–45% of the amine sulfate, compound 6, preferably 40–70% of the hydrochloride (equation III). The mole ratio of amine salt to compound 5 can be from 0.8–3, preferably 1.0–1.35. The mixture is then agitated for 0.5–6 hours at 50°–100°, preferably 85°–95° (equation III). Higher temperatures require shorter reaction times and vice versa. It is important to control the pH between 5.8 and 8.0 during reaction III. If the pH is too low, the reaction will be very slow; if the pH is too high, the product 7 will decompose. By adding the amine in the form of an amine salt 6 and maintaining the pH between 5.8 and 8, a small amount of dissociation of the amine cation results. Thus, during the reaction step represented by Equation III, there is a small amount of free amine present in equilibrium with amine cation. The fact that the reaction rate becomes too slow at low pH indicates that it is important to have a small amount of amine cation dissociated under reaction conditions. This control is most conveniently maintained by using electrodes to monitor the pH and adding base, for example, sodium hydroxide, potassium hydroxide, or calcium hydroxide as needed. Sodium hydroxide is preferred.

It should be realized that in these highly concentrated solutions, pH readings may be only coincidentally related to the hydrogen ion concentration. However, when the meters and electrodes are calibrated against a standard buffer before use, the pH response of the electrodes in the reaction mass indicates the state of the reaction.

The resulting reaction mass contains compound 7 and by-product tri-substituted guanidine as well as unreacted compound 6, all present as salts. Before proceeding with step V it is necessary to convert compound 7 into its free base, compound 9. This also converts unreacted compound 6 into free amine, $HN(CH_3)R_2$, which is removed to prevent the formation of by-product ureas by reaction with compound 10. This operation can be effected by adding 10–50% aqueous sodium hydroxide until the pH is 11.0 to 12.5 as determined by a glass electrode and meter combination and extracting with an organic solvent. Partial distillation of the extract removes the more volatile amine, $HN(CH_3)R_2$. The amine can also be removed directly from the aqueous alkaline solution by distillation. The former procedure is preferred.

The extraction procedure can be performed by passing the aqueous alkaline solution through a continuous counter-current extractor where the organic phase is a solvent which meets the following criteria:

(a) the solvent should be unreactive to water, amines and isocyanates.
(b) the solvent should be only slightly soluble in water; and
(c) the solvent should have a solubility for compound 9 such that it can be readily extracted from the reaction mass.

Examples of suitable solvents are benzene, chlorobenzene, toluene or xylene. Toluene is preferred. A batchwise extraction can also be performed. Temperature can vary between 10° C. and 85° C. The amount of solvent can vary from 0.5 to 10 parts per part aqueous phase, depending on economic factors. The exit organic solvent is sent to a still where amine, $HN(CH_3)R_2$, and any entrained water are distilled overhead, leaving a residual solution of compound 9. The concentration of compound 9 will, of course, depend on the operating parameters of the extractor and still.

The residual solution of compound 9 is analyzed by gas chromatography for tri-substituted guanidine and for compound 9. If any guanidine is present, a stoichiometric amount of 5–10% aqueous sulfuric or hydrochloric acid, preferably sulfuric, is added to form the salt of the guanidine.

Isocyanate 10 is now added. The amount added can vary from 0.8 to 1.0 moles of compound 10 per mole of compound 9; 0.95–1.00 is preferred. The resulting reaction mass is stirred at 10°–90° C., preferably 50°–75° C., until the reaction is complete. Reaction time can be from 0.5 to 8 hours.

If less than a stoichiometric amount of compound 10 has been added, at the end of the reaction the pH is adjusted to 5.5 by adding 5–10% sulfuric or hydrochloric acid; sulfuric is preferred. If acid has been added, the mixture is allowed to settle, and the layers are separated. The lower, aqueous, layer is recycled to the extraction step, and the upper layer is dried by distilling until a constant head temperature is attained either under vacuum or at atmospheric pressure; absolute pressure of 100 to 400 mm Hg is preferred.

If acid is not used, the reaction mass does not have to be distilled. The product 11 can be isolated by concentration and/or cooling of the solution until crystallization occurs followed by filtration or centrifugation. However, it is usually more convenient to carry it forward as a solution to the next step (equation VI).

Even though considerably more stable than the methyl analog, compound 9 (R=ethyl, n-propyl, or isopropyl) is still subject to decomposition in aqueous solution, particularly under conditions of high temperature and pH. Under such conditions it tends to decompose into the corresponding tri-substituted guanidine as illustrated in the following equation:

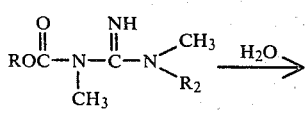

-continued

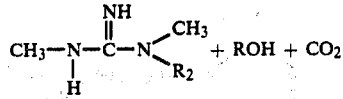

The rate of decomposition is directly proportional to the pH and temperature. Therefore, when removing amine, $HN(CH_3)R_2$, by direct distillation from water, it is preferred to use a vacuum or inert gas to perform the operation as rapidly as possible.

The above-mentioned aqueous distillation procedure can be operated batch-wise or continuously. It is preferred to carry out the operation in a continuous manner so that the exposure of compound 9 to high temperature and high pH is reduced to a minimum. This is accomplished by adding aqueous alkali metal hydroxide to the product from step III in a pipeline reactor or by running the product and an alkali metal hydroxide into a small agitated vessel with a short hold-up time, no more than 10, preferably no more than 2 minutes. The separate flow rates are adjusted so that the resulting pH is between 11.0 and 13.0. If the concentration of amine salt used is such that alkali metal salt precipitates during this neutralization, additional water should be added to maintain this salt in solution. The overflow from this vessel is fed through a distillation column operated under vacuum. The column is heated by feeding steam into the bottom. Amine, $HN(CH_3)R_2$, and water are taken off as distillate overhead and an aqueous solution of compound 9 and tri-substituted guanidine as bottoms.

The conditions under which the column can be operated are numerous and depend to some extent on the substituents present in the amine. However, in general, conditions are selected so that the temperature of the feed through the column is not over 50° C. This necessitates cooling the product from equation III to approximately 30° before adding the caustic. The column is operated at an absolute pressure of 25–300 mm of mercury, preferably 50–150 mm, and the amount of steam fed to the bottom of the column is adjusted such that the amount of water taken overhead along with the amine is equivalent to 5–25% of the weight of the reaction mass from equation IV.

The bottoms from the above distillation are fed into a hold tank which is maintained at a pH of 5–7 by the continuous addition of either sulfuric or hydrochloric acid; hydrochloric is preferred. The concentration of compound 9 in the neutralized solution is maintained at 15–50%, preferably 20–40%. The concentration will depend upon the concentration of the aqueous solution of the amine, the concentration of the base and acid solutions employed in the previous steps, and the amount of concentration or dilution which occurred during the distillation. The temperature of this solution is maintained at 25°–45°, preferably 25°–35°, by either cooling the bottoms in a continuous-type cooler before neutralization or by cooling the neutralization vessel itself.

When the amine has been removed by direct distillation from water, step V is performed by preparing a mixture of the above solution and a solvent as described in detail above in connection with the extraction procedure, such as benzene, chlorobenzene, toluene, or xylene; toluene is preferred. The amount of solvent added should be sufficient to dissolve the amount of compound 11 which will be formed. Generally, the amount of solvent used is about 3–10 times the amount of compound 9 present in the aqueous solution.

An amount of compound 10 which is stoichiometrically equivalent to 85–100%, preferably 95–100%, of compound 9 present in the aqueous layer is now added in one portion or continuously for up to three hours, preferably 30 minutes to one hour and 50% aqueous caustic is added simultaneously with good agitation at a rate which will maintain the pH at 9–10, preferably 9.3–9.7. The caustic addition is continued until the pH is almost constant. The temperature is maintained at 10°–90° C., preferably 35°–50° C., during the addition by external heating and cooling as required. The caustic addition time is from 1–8 hours. The pH is then adjusted to 6.0 with acid. The agitation is stopped and the layers allowed to separate. The lower aqueous layer is removed and the upper organic layer is dried by distilling until a constant head temperature is attained either under vacuum or at atmospheric pressure; absolute pressure of 100–400 mm Hg is preferred.

The solution containing compound 11 can be used as such, or compound 11 can be isolated by crystallization and mixed with a new solvent. Alternatively, the solvent can be exchanged by adding a higher boiling solvent and distilling under reduced pressure so that the pot temperature does not exceed 55° C. Alternatively, a continuous column can be used where the mixed solvent solution is injected into the column, the low boiling solvent taken overhead, and the solution of compound 11 in the high boiling solvent taken as bottoms. If the bottoms are cooled rapidly, the column can be operated as high as 90° C. without significant decomposition of compound 11.

If solvent exchange is used (using either crystallization or distillation) the new solvent must meet the following criteria:

(a) the solvent should be inert with respect to the base used to catalyze the cyclization reaction;
(b) the solvent should allow the by-product alcohol of Reaction VI to be enriched in the overhead upon distillation;
(c) the solvent should have a solubility of at least 5% for compounds 11 and 13; and
(d) the solvent should have a boiling point of from 90° C. to 180° C. at atmospheric pressure.

If solvent exchange is not used, the solvent used in the extraction of compound 9 must also meet the above criteria.

The solution containing Compound 11, however obtained, is then contacted with the ring closure catalyst (Compound 12) to form Compound 13 (Equation VI). The concentration of Compound 11 can vary from 5 to 65%, with 15 to 50% preferred. The initial temperature at which Compound 12 is added can vary from 10° C. to the boiling point of the solvent, however, 25° to 80° C. is a preferred range. The ring closure catalyst is an alkali metal alkoxide or hydroxide. Alkali metal alkoxides can be added either as dry solid or as a solution in the alkanol. Alkali metal hydroxides can be added as a solution in an alkanol. A solution of sodium methoxide in methanol is a preferred catalyst.

The amount of catalyst required varies with the purity of the product. When crystalized compound 11 is used, as little as 0.01 mole percent of catalyst may be sufficient to promote ring closure, however, from 0.1 to 1.0 mole percent of catalyst is generally required. When technical material is used, from 1.0 to 4.0 mole percent is generally required. Catalyst in excess of that required to effect complete reaction should be avoided since it also tends to catalyze the formation of by products.

The role of the catalyst in by product formation is illustrated by the following equation:

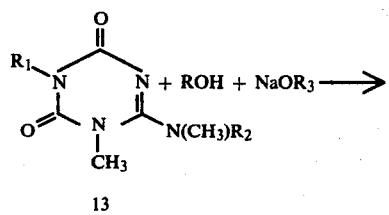

13

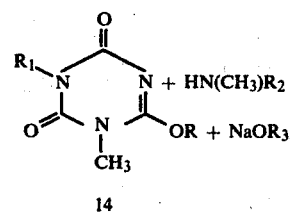

14

The above equation has been written as if only one alkanol is present in the reaction system. However, if sodium methoxide or a solution of sodium methoxide in methanol were used as catalyst and R groups of compound 11 were ethyl or propyl, obviously a mixture of alkanols would be present.

Compound 14 is an alkylating agent and can react with either the alkanol, catalyst or with by product amine to form compound 15, as follows:

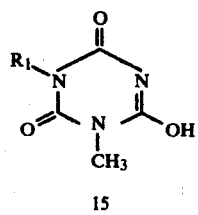

15

Because this compound is acidic, it reacts with the catalyst to form the corresponding sodium salt, which is inactive as a catalyst. Therefore, when an amount of compound 15 is formed equivalent to the catalyst added, all reaction ceases. However, quite high amounts of compound 14 can be formed before this happens.

The reaction may be "frozen" for experimental purposes by adding acetic acid which reacts instantly with the catalyst to stop all reactions. The type of acid is not critical; hence either inorganic or organic acids can be used to convert the catalyst to the inactive salt.

However, the formation of 14 can be suppressed by adding large amounts (2 to 6 moles based on compound 13) of the amine used in Reaction III to the reaction mass before addition of the catalyst. This reduces the yield of compound 14 by converting it back to compound 13 in a dynamic equilibrium as illustrated in the following equation:

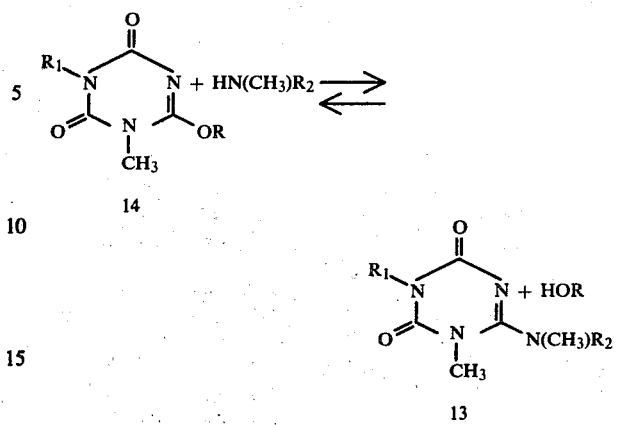

Therefore, regardless of how long the reaction is allowed to proceed, only the equilibrium concentration of compound 14 is formed. However, the use of large amounts of amine results in serious process complications. The amine must be fractionated from the reaction mass, condensed (when $R_2$ = methyl or ethyl, expensive refrigeration is required), stored and recycled. In addition, there may be pollution problems associated with handling amines.

A superior method of reducing the amount of compound 14 formed during the reaction is to remove the by-product alkanol substantially as it is formed. When this is done, it is no longer available to enter into the reaction with the triazine-dione product to form compound 14 or to react with compound 14 to form compound 15. Therefore, by-product formulation is reduced and less catalyst is required.

In order to achieve rapid removal of by-product alkanol during the cyclization step, substantially as it is formed, it is, of course, also necessary to mix the catalyst with compound 11 as rapidly as possible. Because good mixing is very difficult to obtain in large-scale batch equipment, it will be recognized by those skilled in mixing operations that continuous mixing will be preferred. Mixing of the cyclization catalyst with compound 11 can be accomplished by mixing in a short residuence time mixer, such as a pipeline mixer, prior to introduction into whatever vaporization means is used. It is preferred that the reaction dispersion of compound 11 and catalyst be passed to the vaporization means within 10–15 milliseconds after initial contact.

It is preferred that the vaporization means be operated in such manner that essentially complete alkanol removal is achieved within about 120 seconds and preferably within no more than about 60 seconds. In a continuous distillation column operation, it is preferred to have a stream of solvent vapor passing up through the column at a rate such that the quantity of overhead product is equal to 0.2–1.2 (preferably 0.4–0.8) times the reaction mass entering the system. By this means, there is sufficient boil-up to accomplish rapid and complete removal of the by-product alkanol. The precise operating temperature and pressures used for vaporization of the alkanol will depend upon the particular reactants and solvents utilized and are thus within the skill of one familiar with the fractionation art.

Though it is not essential to the practice of the invention, it may be preferred to add acid to the dispersion of catalyst after alkanol removal is terminated. In consideration of the rapid rate of the cyclization reaction and alkanol formation, this will normally be subsequent to essential complete removal of the alkanol. This serves (1) to deactivate the catalyst thus preventing the reaction of even trace amounts of alkanol which may still be present, and (2) to prevent decomposition reactions during recovery of the desired compound 13. The amount of acid should be at least about equivalent to the number of moles of catalyst remaining in the system.

Compound 13 is isolated from the liquid residue by conventional procedures, such as the following:

The residue is washed at 30°-100° C., preferably 50°-70° C., with water. The layers are allowed to settle, the aqueous layer is removed. This washing procedure removes the salt of 15 which is formed during the ring-closure reaction. If a less pure product is satisfactory, the washing step can be eliminated.

The product can be isolated from the organic solvent either after the washing operation or without washing in a number of ways as described below:

(a) The organic phase is concentrated by distillation and is then diluted with a poor solvent for compound 13, e.g., hexane, which causes compound 13 to precipitate. The stable crystalline product is recovered by conventional methods.

(b) The organic phase is concentrated past the solubility limit of compound 13 and is then seeded with crystalline compound 13. An aqueous brine, such as 20% sodium chloride is added, and the organic solvent is boiled off as an aqueous azeotrope at 50-100 mm. Hg. absolute pressure. The aqueous phase of the azeotrope is returned to the vessel. Compound 13 continues to crystallize as the solvent is removed. When solvent removal is complete, the resulting 10-30% slurry is filtered or centrifuged warm at 38°-80°, preferably 40°-45°, washed with water, and the resulting wet cake is dried, thus giving stable crystalline compound 13.

(c) All of the solvent is removed from the organic phase by distillation and sparging with nitrogen or steam at approximately 125°. The compound 13 melt is picked up by a transfer roll and deposited on an agitated, hot (70°-100°, preferably 80°) flaker drum. The flake is then scraped and collected by a heated (60°-80°) screw conveyor. The warm stable crystalline 13 is then permitted to cool to ambient temperature.

(d) Instead of flaking the compound 13 melt described in (c) above, the melt is fed to an agitated, jacketed vessel, such as a "Sigma Arm" mixer, or an agitated, heate fluidized bed of compound 13 crystals, where vigorous agitation is maintained while the temperature is held slightly below the melting point of compound 13, thus giving stable crystalline compound 13. In addition, a solution or slurry of compound 13 can be applied to an agitated, heated fluidized bed of compound 13 crystals. The solvent is permitted to evaporate and the particles of compound 13 increase in both number and size.

In the following example, all parts are by weight and all temperatures in degrees centigrade unless otherwise indicated.

EXAMPLE

A. Synthesis N-ethoxycarbonyl-N-methylcyanamide (Equations I and II)

657 Parts of ethylchloroformate and 945 parts of a 50% aqueous sodium hydroxide solution were added simultaneously to a solution of 504 parts of a 50% aqueous cyanamide solution in 825 parts of water at 25° during a period of 90 minutes and at a pH of 6.9 to 7.1. As the addition of the reactants progressed, the temperature of the reaction mass was allowed to rise to 53°-55° and was maintained within that range by cooling. When the addition was complete, the reaction mass was cooled to 40°. Dimethylsulfate (1,134 parts) was then added during one hour with stirring while maintaining the pH at 7 to 7.1 by the addition of 50% aqueous sodium hydroxide solution. After holding 3 hours at 40° the resulting two-phase solution was transferred to a separatory funnel. The upper phase of N-ethoxycarbonyl-N-methylcyanamide was separated and the lower aqueous phase was sent to secondary recovery, either distillation or extraction. The upper phase of 669 parts was 93% N-ethoxycarbonyl-N-methylcyanamide (81% yield). This upper phase is usually pure enough for subsequent steps. However, vacuum distillation was used to provide pure N-ethoxycarbonyl-N-methylcyanamide, b.p. 67° at 2.2 mm.Hg.

By the above procedure and using equivalent molecular weights of isopropyl or n-propyl chloroformates, the following n-propoxycarbonyl- or isopropoxycarbonyl-N-methylcyanamide can be prepared:
N-isopropoxycarbonyl-N-methylcyanamide
N-propoxycarbonyl-N-methylcyanamide B. Synthesis of N-ethoxycarbonyl-N,N',N'-trimethylguanidine (Equations III and IV)

A solution of 339 parts of dimethylamine hydrochloride in 500 parts of water was heated to 50° and 458 parts of the upper phase from (A) was added to it. The resulting two-phase mixture was then heated for approximately 2.25 hours at 90° and pH of 6.5, after which time the starting N-ethoxycarbonyl-N-methylcyanamide had nearly completely disappeared. The pH was kept at 6.5 by adding 50% sodium hydroxide as required. The solution was then cooled to 40° and 25% aqueous sodium hydroxide solution was added to reach pH 11.5. Repeated extraction of the reaction solution with toluene and partial evaporation of the toluene gave a solution containing 489 parts of crude N-ethoxycarbonyl-N,N',N'-trimethylguanidine from which the pure product was isolated by distillation at 70°/0.3 mm.Hg.

By the above procedure using equivalent molecular weight amounts of the appropriate amine hydrochloride or amine sulfate and n-propoxy- or isopropoxy-carbonyl-N'-alkylcyanamide, the following intermediate guanidines can be prepared:
N-propoxycarbonyl-N-methyl-N'-isopropyl-N'-methylguanidine   N-isopropoxycarbonyl-N-methyl-N'-isopropyl-N'-methylguanidine C. Synthesis of Ethyl N-(N-cyclohexylcarbamoyl-N',N'-dimethylamidino)-N-methylcarbamate (Equation V)

11 Parts of cyclohexyl isocyanate was added to 16 parts of N-ethoxycarbonyl-N,N',N'-trimethylguanidine in 150 parts of toluene. The temperature was kept at 50° to 75° for 1.25 hours to complete the reaction. The product, ethyl-N-(N-cyclohexylcarbamoyl-N',N'-dimethylamidino)-N-methylcarbamate was isolated by crystallization, filtration, and drying, m.p. 97°-98°. Preferably, however, it is kept as a toluene solution and carried forward as such to the next step (Equation V).

Following the general method of Example C using the appropriate isocyanate with the appropriately substituted alkoxycarbonylguanidine, the following compounds can be prepared:

Ethyl N-(N-cyclopentylcarbamoyl-N',N'-dimethylamidino)-N-methylcarbamate

Isopropyl N-[N-(3-methylcyclohexylcarbamoyl)-N',N'-dimethylamidino]-N-methylcarbamate Propyl N-(N-cyclohexylcarbamoyl-N'-butyl-N'-methylamidino)-N-methylcarbamate

D. Synthesis of 1-methyl-3-cyclohexyl-6-dimethylamino-s-triazine-2,4(1H,3H)dione (Equations II, III, IV, V)

A 50% stoichiometric excess of dimethylsulfate (1234 parts) was added at 40° during one hour with agitation to 3141 parts of an aqueous solution containing 888 parts of the sodium salt of compound 3 (R=ethyl) which had been adjusted to pH 7 with 50% aqueous sodium hydroxide. The reaction was allowed to continue for three hours while the temperature was maintained at 40° by external heating or cooling and at pH 7 by the addition of 50% aqueous sodium hydroxide as required. During the reaction a separate phase of compound 5 (R=ethyl) was formed.

When the reaction was about complete, the agitation was stopped and the layers allowed to separate. The upper layer of 728 parts was 93% pure compound 5 (R=ethyl). It was separated and added to 1,200 parts of an aqueous solution containing 540 parts of dimethylammonium chloride. The resulting mixture was heated to 90° and stirred for 2.25 hours at pH 6.5. The pH was maintained at 6.5 by adding 50% sodium hydroxide as required. The solution was then fed into a mixing tee along with 25% aqueous sodium hydroxide. The separate feed rates were adjusted so that the effluent from the tee was kept at pH 11.0–11.5. The effluent from this vessel was fed into the top of a continuous counter-current extractor, which operates as a 5 theoretical plate column. Toluene was fed into the bottom of the column at a rate of 2.25 parts of toluene per part of aqueous feed. The toluene solution at the top of the column overflows into an amine stripper.

In the stripper, excess dimethylamine, entrained water, and some toluene solvent are distilled overhead through a packed column. The residual toluene solution of 7743 parts contained 777 parts of compound 9 ($R_2$=methyl; R=ethyl). Analysis showed by-product 1,1,3-trimethylguanidine to be present in this residue, and a small amount of sulfuric acid solution was added to exactly neutralize all of the 1,1,3-trimethylguanidine but little or none of compound 9.

507 Parts of cyclohexylisocyanate was added to this residue. The mixture was then stirred at 50°–75° for 1.25 hours. It was cooled to 40° and sulfuric acid solution was added with good stirring until the pH of the aqueous phase was 5.5. The organic phase was separated and concentrated by distillation at a pressure of 100 mm. The organic phase of 4017 parts contained 1,205 parts of compound 11 ($R_2$=methyl; $R_1$=cyclohexyl; R=ethyl).

A 25% solution of sodium methoxide in methanol (16.5 parts) was injected into the well-agitated solution of compound 11 at 50° C. The temperature increased to 58.6° C. in 20 seconds; after an additional 70 seconds, 5.4 parts of glacial acetic acid was added. The solution was then evaporated to dryness in a 50° C. vacuum oven to give 1027 parts of a product that contained 914 parts of compound 13 ($R_1$=cyclohexyl; $R_2$=methyl) by gas chromatographic analysis. This material can be worked up to a stable solid product by heating to 125° C. and flaking or by adding to a fluidized bed of compound 13.

E. Alternate Synthesis of 1-Methyl-3-cyclohexyl-6-dimethylamino-s-triazine-2,4(1H,3H)dione (Equation II)

A solution containing 1205 parts of compound 11 and 2812 parts of toluene was prepared as described in D above. While the reaction mass was being distilled at 111 mm Hg, 11.5 parts of a 25% solution of sodium methoxide in methanol was injected into it. The rate of distillation increased rapidly from 35 parts/min to 350 parts/min while the pot temperature dropped from 58.1° to 49.2° in 50 seconds. After an additional 70 seconds, 3.2 parts of acetic acid was added. The solution was then evaporated to dryness in a 50° C. vacuum oven to give 1025 parts of a product containing 964 parts of compound 13 ($R_1$=cyclohexyl; $R_2$=methyl). This material can be worked up to stable solid product by heating to 125° C. and flaking or by adding to a fluidized bed of compound 13.

F. Alternate Synthesis of 1-Methyl-3-cyclohexyl-6-dimethylamino-s-triazine-2,4(1H,3H)dione (Equation V)

A toluene solution containing 1205 parts of Compound 11 in 7200 parts of solution was prepared as in D above by stopping the distillation in an earlier stage.

Dimethylamine (1,095 parts) was added to the solution of compound 11 while the temperature was maintained at 25°–50° by external cooling. Then 35 parts of a 25% solution of sodium methoxide in methanol was added with good agitation. The reaction is slightly exothermic and the temperature increased 4° during 15–45 seconds. The reaction was allowed to continue for an additional ten minutes; then 9.72 parts of acetic acid were added. The solution was then distilled until a constant 110° head temperature showed that dimethylamine and by-product alkanols have been completely removed. The still bottoms were cooled to 60° and washed with a small quantity of 5% sodium hydroxide followed by a small quantity of water. The amount of sodium hydroxide was calculated so that it was equivalent in moles to the acetic acid added earlier.

The toluene phase was then concentrated by distillation until the concentration of compound 13 ($R_1$=cyclohexyl; $R_2$=methyl) reached 50% by weight. The residue was cooled to 40° and stirred while n-hexane was added slowly.

The weight of n-hexane used was 80% of the total weight of the 50% solution. During the n-hexane addition the solution was seeded with compound 13. The crystals were recovered by filtration and dried to give 920 parts of compound 13 ($R_1$=cyclohexyl; $R_2$=methyl), m.p. 112°–115° C.

The following s-triazinediones are prepared by cyclization of the appropriate alkoxy-N-(N-substituted carbamoyl-N',N'-dialkylamidino)-N-methylcarbamate by the above procedure:

1-Methyl-3-cyclopentyl-6-dimethylamino-s-triazine-2,4(1H,3H)-dione, m.p. 126°–129°

1Methyl-3-cyclohexyl-6-(N-butyl-N-methylamino)-s-triazine-2,4(1H,3H)dione

1-Methyl-3-(4-chlorophenyl)-6-dimethylamino-s-triazine-2,4-(1H,3H)dione

G. Alternate synthesis of Ethyl N-(N-cyclohexylcarbamoyl)-N',N'-dimethylamidino)-N-methylcarbamate (Equation IV)

A solution of the hydrochloride salt of compound 7 as prepared in example B above is adjusted to pH 12.3 with 25% sodium hydroxide. The alkaline solution is then fed to the top of an amine stripper column where it flows downward against a counter-current nitrogen stream. The outflow at the bottom is acidified to pH 5.5 as soon as it exits from the column. The collected outflow is added to 7,000 parts of toluene. The pH of the well agitated solution is adjusted to and maintained at 9.5 by the addition of 50% aqueous sodium hydroxide while 470 parts of cyclohexyl isocyanate is added during one hour. The sodium hydroxide addition is continued for an additional three hours or until the pH becomes almost constant at 9.5. At this time the pH is adjusted to 5.5. The temperature is maintained at 50° throughout the reaction. The lower aqueous layer is removed and the upper toluene layer is worked up as in example C to give ethyl N-(N-cyclohexylcarbamoyl-N',N'-dimethylamidino)-N-methylcarbamate in about the same yield.

H. Synthesis of 1-Methyl-3-cyclohexyl-6-dimethylamino-s-triazine-2,4(1H,3H)-dione without alcohol removal-batch operation (Equation VI)

A 25% solution of sodium methoxide in methanol (16.5 parts) was injected into a well-agitated solution containing 1205 parts of compound 11 (R=ethyl; $R_1$=cyclohexyl; $R_2$=methyl), prepared as described in the Example, section D in said U.S. Ser. No. 574,351, at 50° C. The temperature increased to 58.6° C. in 20 seconds; after an additional 70 seconds, 5.4 parts of glacial acetic acid was added. The solution was then evaporated to dryness in a 50° C. vacuum oven to give 1027 parts of a product that contained 914 parts (89.7% of theory) of compound 13 ($R_1$=cyclohexyl; $R_2$=methyl) by gas chromatographic analysis. This material can be worked up to stable solid product by heating to 125° C. and flaking or by adding to a fluidized bed of compound 13.

I. Synthesis of 1-Methyl-3-cyclohexyl-6-dimethylamino-s-triazine-2,4(1H,3H)-dione with continuous alcohol removal (Equation VI)

A solution of 25% wt. of compound 11 (R=ethyl; $R_1$=cyclohexyl; $R_2$=methyl) in toluene at 55°-60° C. was mixed at a rate of 650 ml/min. with 3.0–3.5 ml/min. of an 18% (wt.) solution of sodium methoxide in methanol* at room temperature utilizing a mixing tee. The mixing tee located just outside the top plate of a 6-inch diameter 9-tray sieve plate column, provided turbulent mixing of the two streams, and required less than 50 milliseconds to discharge the mixture to the top tray of the column. The column was operated at 100 mm Hg pressure above the top tray. Toluene was continuously vaporized at the rate of 283 ml/min. outside the column and was introduced into the column as 90° C. vapor below the bottom (9th) tray.

*(1.7-1.9 mole %)

These feed and boil-up rates and temperatures gave about 320 ml/min overhead (distillate) and 620 ml/min bottoms (product) rates. The holdup time of liquid in the column was estimated to be less than 4 minutes. About 5.5 ml/min of glacial acetic acid was added to the product receiver.

The above conditions translate to mass ratios of vapor/feed of 0.40 and distillate/feed of 0.45 and a catalyst level of 2 mole percent based on compound 11.

Analysis of the reaction product by gas chromatography showed the yield of compound 13 was 97.2% of the theoretical yield from compound 11.

Additional s-triazinediones, which can be prepared by the process of the invention using the appropriate alkoxy-N-(N-substituted carbamoyl-N',N-dialkylamidion)-N-methylcarbamate, are illustrated by the following:

1-Methyl-3-cyclopentyl-6-dimethylamino-s-triazine-2,4(1H,3H)-dione, m.p. 126°-129°

1-Methyl-3-cyclohexyl-6-(N-butyl-N-methylamino)-s-triazine-2,4(1H,3H)-dione

1-Methyl-3-(4-chlorophenyl)-6-dimethylamino-s-triazine-2,4(1H,3H)-dione.

What is claimed is:

1. A process for preparing a triazine compound of the formula:

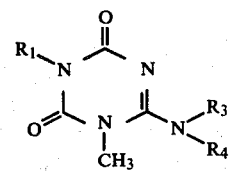

wherein
$R_1$ is $C_2$-$C_8$ alkyl, $C_5$-$C_8$ cycloalkyl, norbornyl, methylcyclohexyl, methylcyclopentyl, phenyl, or chlorophenyl;
$R_3$ is methyl; and
$R_4$ is $C_1$-$C_4$ alkyl;
said process comprising the following steps in sequence:
(a) contacting cyanamide with a $C_{2-3}$ alkyl chloroformate to form the corresponding alkoxycarbonylcyanamide;
(b) contacting said alkoxycarbonylcyanamide with an alkylating agent of the formula $CH_3Z$ to form the corresponding N-alkoxycarbonyl-N-methylcyanamide;
(c) contacting said N-alkoxycarbonyl-N-methylcyanamide at a pH of 5.8–8.0 with an amine salt of the formula:

where
$Y = Cl^-$ or $SO_4^{--}$,
$n = 1$ when $Y = Cl^-$, and
$n = 2$ when $Y = SO_4^{--}$,
to form a compound of the formula:

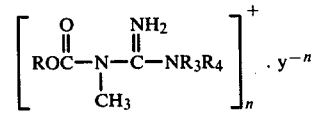

(d) contacting the product compound of step (c) with and alkali metal hydroxide to form a compound of the formula:

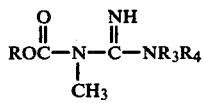

containing unreacted amine;

(e) removing unreacted amine, R$_3$R$_4$NH from the reaction product compound of step (d) by extraction of the product compound containing unreacted amine into an inert organic solvent and removal of unreacted amine from the extract by vaporization therefrom, (f) contacting the product compound of step (e), from which the amine has been removed, with an isocyanate of the formula R$_1$NCO to form a compound of the formula:

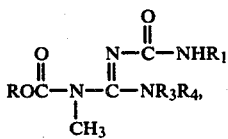

(g) rapidly admixing a base N'OR$_5$ with amine-free product of step (f) by which the reaction product compound is cyclized to form triazine compound having the above formula and by-product alkanol and rapidly removing by-product alkanol from the cyclized reaction product by vaporization therefrom.

2. Process of claim 1 wherein R=ethyl.

3. Process of claim 1 wherein R=ethyl.

4. Process of claim 2 where the reaction product of step (g) is isolated by crystallization induced by adding hexane to a solution of said reaction product in toluene.

5. Process of claim 1 wherein the distilled extract resulting from step (e), which contains the desired reaction product of step (d), is contacted with aqueous acid before proceeding with step (f).

6. Process of claim 2 wherein the unreacted amine, HN(CH$_3$)R$_2$, is removed from the reaction mass resulting from step (d) by aqueous distillation.

7. Process of claim 6 wherein the reaction mass resulting from the aqueous distillation is contacted with an amount of aqueous acid sufficient to neutralize any base present therein.

8. Process of claim 2 wherein the unreacted amine and the product of step (d) are removed from the reaction mass resulting from step (d) by batch or continuous extraction with toluene and the amine is separated from the reaction product of step (d) by distillation of the toluene extract, prior to contacting the reaction product with isocyanate.

9. Process of claim 8 wherein the distilled extract, which contains the desired reaction product of step (d), is contacted with aqueous acid before proceeding with step (f)

10. Process of claim 2 wherein the reaction mass resulting from step (f) is contacted with aqueous acid before preceeding with step (g).

11. Process of claim 10 wherein the aqueous acid is selected from the group consisting of hydrochloric and sulfuric.

12. Process of claim 10 wherein said aqueous acid is added in an amount sufficient to lower the pH of the reaction mass to about 5.5.

13. The process of claim 1 in which the removal of by-product alkanol is carried out in a continuous distillation column.

14. The process of claim 13 in which the removal of by-product alkanol from the cyclization reaction product in step (g) is completed within 120 seconds after the reactant compound and catalyst are contacted.

15. The process of claim 1 in which the s-triazine reaction product is 1-methyl-3-cyclohexyl-6-dimethylamino-s-triazine-2,4(1H,3H)-dione.

* * * * *